(12) United States Patent
Scherhag et al.

(10) Patent No.: US 6,809,076 B2
(45) Date of Patent: Oct. 26, 2004

(54) USE OF ANTICOAGULANT AGENTS IN THE EXTRACORPOREAL TREATMENT OF BLOOD

(75) Inventors: Rudi Scherhag, Schriesheim (DE);
Peter Bacher, Neuhofen (DE);
Christopher Parow, Speyer (DE);
Hans-Ulrich Esslinger, Nussloch (DE);
Florian Abel, Stuttgart (DE)

(73) Assignee: Abbott GmbH & Co. KG (DE)

(*) Notice: Subject to any disclaimer, the term of this patent is extended or adjusted under 35 U.S.C. 154(b) by 27 days.

(21) Appl. No.: 09/811,410

(22) Filed: Mar. 20, 2001

(65) Prior Publication Data

US 2002/0039994 A1 Apr. 4, 2002

Related U.S. Application Data

(60) Provisional application No. 60/190,103, filed on Mar. 20, 2000.

(30) Foreign Application Priority Data

Mar. 20, 2000 (EP) .............................................. 00105867

(51) Int. Cl.$^7$ .............................................. A61K 38/28
(52) U.S. Cl. ........................................................ 514/4
(58) Field of Search ................... 514/4, 2, 12; 530/350, 530/324, 410

(56) References Cited

U.S. PATENT DOCUMENTS

| 5,256,559 A | * 10/1993 | Maraganore et al. | .......... 514/12 |
| 5,362,858 A | * 11/1994 | Bischoff | .................... 530/345 |
| 5,368,555 A | * 11/1994 | Sussman et al. | .......... 604/6.05 |
| 5,538,946 A | 7/1996 | Crause et al. | .................. 514/12 |
| 5,663,141 A | * 9/1997 | Kurfuerst et al. | ............. 514/12 |
| 5,705,355 A | 1/1998 | Tolstoshev et al. | ........... 453/13 |
| 5,723,576 A | * 3/1998 | De Rosa et al. | ............ 530/324 |
| 6,492,336 B1 | * 12/2002 | Mahiout | ...................... 514/25 |

FOREIGN PATENT DOCUMENTS

| CA | 2369096 A1 | * 10/2000 | .......... A61K/31/00 |
| DE | 19915862 A1 | * 10/2000 | .......... A61K/31/00 |
| EP | 372 670 | 6/1990 | |
| WO | 98/46649 | 10/1998 | |

OTHER PUBLICATIONS

Fischer KG, van de Loo A, Bohler J. Recombinant hirudin (lepirudin) as anticoagulant in intensive care patients treated with continuous hemodialysis.Kidney Int Suppl. Nov. 1999;72:S46–50.*

Esslinger et al. "Pharmacodyamic and Safety Results of PEG–Hirudin in Healthy Volunteers" Thromb. Haemost vol. 77 No.5(1997) pp. 911–919.

Esslinger et al. "Pharmacokinetics of PEG–hirudin in subjects with various degrees of renal functions" Ann. of Hematol. vol. 76 (1998) pp. A97.

Beirjering et al. "Anticoagulants and Extracorporeal Circuits" Seminars in Thrombosis and Hemostatis vol. 23 No. 2 pp. 225–233 (1997).

Mehta et al. "Anticoagulation During Continuous Renal Replacement Therapy" ASAIO Journal (1994) pp. 931–935.

Schmidmeier et al. "A New Biodegradable Polylactic Acid Coronary Stent–Coating, Releasing PEG–Hirudin and a Prostacycline Analog,Reduces Both Platelet Activation and Plasmatic Coagulation" Journal of the American College of Cardiology vol. 29 No. 2 (1997) pp. 354A.

Cli.Chem.Lab.Med., 1998,vol. 36, No. 11,847–854,Heidrich.

XP–002068341,Schmidmaier et al.

* cited by examiner

*Primary Examiner*—Karen Cochrane Carlson
*Assistant Examiner*—Sheridan K Snedden
(74) *Attorney, Agent, or Firm*—Keil & Weinkauf

(57) ABSTRACT

The present invention relates to the use of anticoagulant agents for the treatment of individuals with extracorporeal circulation as anticoagulant during the extracorporeal circulation and for prophylaxis of vascular complications after the extracorporeal circulation. It is thus possible in particular to treat individuals with chronic renal insufficiency requiring regular hemodialysis and moreover prevent vascular complications which, on use of conventional anticoagulants, result in a high morbidity and mortality rate for dialysis patients treated longer-term.

9 Claims, 4 Drawing Sheets

USE OF ANTICOAGULANT AGENTS IN THE EXTRACORPOREAL TREATMENT OF BLOOD

Figure 1:
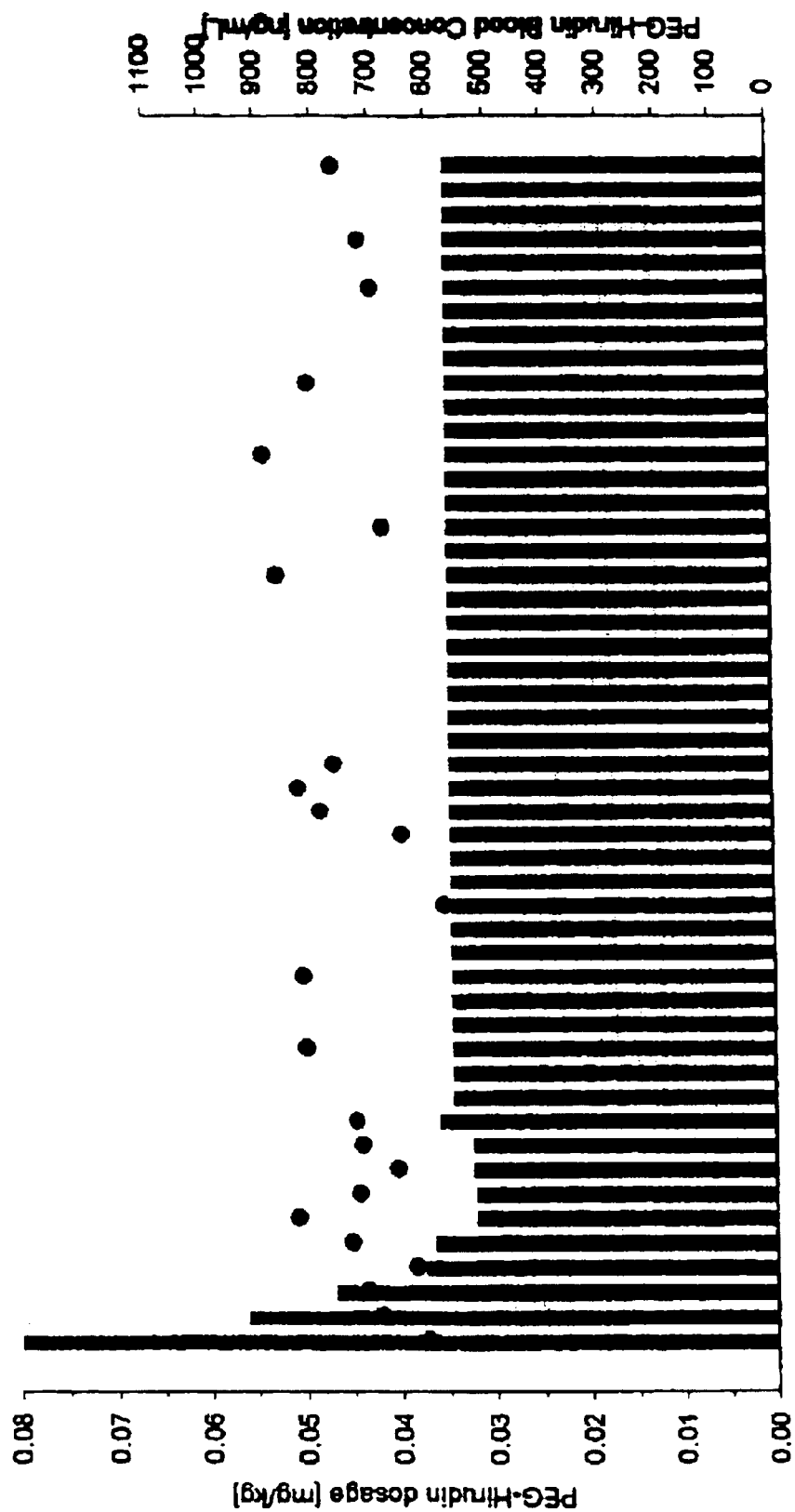

This application claims benefit of 60/190,103 filed Mar. 20, 2000.

The present invention relates to the use of anticoagulant agents in the extracorporeal treatment of blood.

Blood in an extracorporeal circulation comes into contact with exogenous surfaces. This activates the blood coagulation system, for example factor XII and blood platelets via the intrinsic pathway of the coagulation cascade. The blood coagulates. The prevention of this is the task of the anticoagulants which are conventionally administered in this situation.

In clinical practice it is virtually always heparin and heparin-like agents which are employed for this purpose, although there are problems with the use thereof. Patients treated with heparin need continuous monitoring in particular because of the generally known risk of HIT, osteoporosis, lipid metabolism disturbances and bleeding complications. It is often necessary to comply with a complicated dosage regimen. Thus, after an initial bolus of 10–20 U/kg, the patients usually receive a further 5–10 U/kg/h in order to maintain a predetermined level in the blood (Mehta R. L., ASAIO Journal, 931–935 (1994)).

In view of these disadvantages there has been a search for favorable alternatives to heparin, and the so-called low molecular weight heparins in particular were found, and these provide not only a prolonged half-life in the blood but also an increased aXa/aIIa ratio. Experiments with other glycosaminoglycans, for example heparan sulfate, dermatan sulfate, chondroitin sulfate and mixtures thereof, were aimed in the same direction. Thus, for example, orgaran has an aXa/aIIa ratio of 22, whereas most low molecular weight heparins are in the range from 1 to 5 (Beijering et al., Seminars in Thrombosis and Hemostasis, Vol. 23, No. 2, 225–233 (1997)).

A corresponding search for a prolonged half-life was successful with hirudins. In contrast to the glycosaminoglycans discussed above, these are peptides, for example natural hirudin obtained from the salivary glands of the medical leech Hirudo medicinalis, or recombinant hirudin. In this connection too, there have been attempts to counteract the relatively short residence time of hirudins in the animal or human body, for example with the aid of derivatized hirudins. In this sense, EP 0 345 616 describes dextran- and Sepharose-derivatized hirudin. The pegylated hirudin muteins described in EP 0 502 962 were also developed with the aim of achieving even longer half-lives, with undiminished activity.

Because of their anticoagulant activity, the substances described above can always be beneficial when anticoagulation is desired. Thus, EP 0 502 962 mentions—in this case for PEG-hirudin—the indications typically listed for anticoagulants, including precisely their use during extracorporeal blood circulation, for example in a hemodialysis or a cardiopulmonary bypass.

Despite the effective protection during the actual dialysis, there is an increasing frequency of reports of a disproportionately high incidence of vascular complications especially in patients with chronic kidney disease. Concerning the occurrence of serious vascular complications, statistical surveys indicate a high risk of 20–30% a year for dialysis patients receiving long-term treatment. About 40–50% of all artifical accesses (shunts) implanted as junction between extracorporeal circulation and vascular system in the USA have to be renewed each year because of a diminution of function (for example through blockage). The mortality rate owing to vascular complications in these hemodialysis patients is about 12% a year. This contributes to the average survival being only 6 years for patients with chronic kidney disease, even with regular hemodialysis. This survival correspond s to that for a metastasizing oncosis.

The object on which the present invention is based, of more comprehensive protection of patients with an extracorporeal circulation and, in particular, dialysis patents receiving long-term treatment, is achieved by the combined therapeutic and prophylactic use of anticoagulant agents.

The present invention therefore relates to the use of anticoagulant agents for the treatment of individuals with an extracorporeal circulation as anticoagulant during the extracorporeal circulation and for prophylaxis of vascular complications after th e extracorporeal circulation.

The treatment period is divided according to the invention into treatment phases in which the blood of the individual to be treated passes through an extracorporeal circulation (extracorporeal treatment phases), and into treatment phases in which the blood is not passed through an extracorporeal circulation (intracorporeal treatment phases).

An extracorporeal circulation means diverting the blood outside a n individual's body. The aim is usually to exclude sections of the body from the bloodstream and/or perform an extracorporeal treatment of the blood. The former use is indicated in particular in operations on the open heart or on major blood vessels, for example for temporary disconnection of the heart by means of a cardiopulmonary bypass (heart-lung machine). The latter use is particularly indicated for extrarenal kidney-function treatment of blood, for example by hemodialysis in cases of renal insufficiency or by hemofiltration in cases of renal insufficiency or other conditions, for example in patients undergoing lipid apheresis.

When blood is in an extracorporeal circulation there is contact between blood or blood constituents and surfaces of the extracorporeal system, which may lead inter alia to an activation of blood coagulation. From the medical viewpoint, this circumstance makes anticoagulant measures necessary, which are aimed in particular at the extracorporeal system during the extracorporeal phase. Anticoagulant agents are used according to the invention as anticoagulant for this purpose. The anticoagulant effect relates in this connection in particular to the prevention of thrombus formation and, where appropriate, diminution of thrombus growth especially in the extracorporeal system.

It is additionally possible to take further expedient anticoagulant measures during the extracorporeal phase on use of a particular anticoagulant agent. The expediency of and necessity for further anticoagulant measures are subject to expert assessment. Thus, further anticoagulants in addition to a particular anticoagulant agent may be used within the framework of further anticoagulant measures. A particular type of further anticoagulant measures may comprise equipping extracorporeal systems or parts thereof with anticoagulants, for example, coating surfaces.

The term "anticoagulant" has the generally accepted meaning for the purpose of the invention. Accordingly, the anticoagulant agents include accepted anticoagulants and agents with a similar effect on blood coagulation of vertebrates, preferably mammals and, in particular, humans.

A particular class of anticoagulant agents comprises the direct thrombin inhibitors, for example hirudins and hirudin, derivatives, especially PEG-hirudin.

In one aspect of the present invention, anticoagulant agents with an extended half-life in the organism to be treated are advantageous for particular treatment regimens according to the invention. Preferred according to the invention for this purpose are anticoagulant agents with a longer half-life than heparins and, in particular, unfractionated heparins and, especially, those with a terminal half-life after intravenous administration of at least about 4 h, even better of at least about 5 h and, in particular, of at least about 6 h. The stated terminal half-lives relate to essentially intact kidney function, that is to say normally a renal elimination efficiency corresponding to a creatinine clearence [sic] $CL_{CR}$ of at least about 100 ml/min.

In another aspect of the present invention, anticoagulant agents with an enduring pharmacodynamic activity in the organism to be treated are advantageous for particular treatment regimens according to the invention. Agents with pharmacodynamic activity are those which according to the invention have minimal prophylactic activity, i.e. bring about a clinically relevant reduction of vascular complications compared with an untreated control group. Enduring means, in particular, a time span which extends beyond the extracorporeal phase and, specifically in the case of a regular alternation of extra- and intracorporeal phases, advantageously extends to the next extracorporeal phase.

The half-life and pharmacodynamics of an anticoagulant agent not only depend on the agent chosen but may also be controlled, for example, by pharmaceutical measures. Thus, agents with a short half-life or pharmacodynamic activity per se can be administered as suitable slow-release formulation.

Anticoagulant agents with a delayed action are described, for example, in EP 0 345 616 which relates to particular hirudin derivatives composed of hirudin and soluble carriers.

The use of an anticoagulant agent with an extended half-life and an enduring pharmacodynamic activity offers the advantage of being used both as anticoagulant during the extracorporeal circulation and for prophylaxis of vascular complications after the extracorporeal circulation. Thus, it is preferred to carry out the treatment according to the invention with a single agent.

The use of PEG-hirudin is particularly preferred according to the invention. PEG-hirudin stands for polyethylene glycol conjugates of hirudin. The term hirudin refers here to a class of polypeptide-based anticoagulant substances which are derived from true hirudin, the natural polypeptide which can be isolated from the medical leech Hirudo medicinalis. Thus, the term hirudin according to the invention also includes recombinant variants (r-hirudin) as well as mutated variants (hirudin muteins). Prefered for the polyethylene glycol conjugation are the polypeptides of the formula II described in EP 0 502 962 and, of these, in particular the polypeptide with the sequence SEQ ID NO:1 according to the invention. The polyethylene glycols are preferably conjugated via lysine residues, where appropriate using suitable linkers, for example those indicated in EP 0 502 962, which are advantageously stable under physiological conditions.

It is particularly preferred according to the invention to use PEG-hirudin based on the polypeptide described above with the sequence SEQ ID NO:1, to which a polyethylene glycol residue is bound in each case to the lysine in position 27 and the lysine in position 33. The binding can take place, for example, via a urethane-like linker. Polyethlyene [sic] glycol residues of the formula

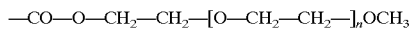

in which n is an integer from 50 to 200, preferably from 75 to 150 and, in particular, from 110 to 120, which are bound to the ∈-amino group of lysine residues are preferred. Accordingly, the term PEG-hirudin refers to a usually heterogeneous mixture of pegylated peptides with varying polyethlyene [sic] glycol residues. The variation in the polyethlyene [sic] glycol residues is attributable in particular to a variation in the PEG chain length, whose molecular weight varies in accordance with the value of n in a range from about 2000 to about 9000, preferably from about 3000 to about 7000 and, in particular, about 5000 +/−1000 Da.

According to one aspect of the present invention, one embodiment of PEG-hirudin has a weight average molecular weight, determined by exclusion chromatography (Superose 12, calibrated with PEG, Pharmacia), of about 17,000 +/−1000 Da.

According to another aspect of the present invention, an advantageous embodiment of PEG-hirudin has a specific antithrombotic activity of about 10,000–14,000 ATU/mg of protein.

There are several possibilities for connecting the extracorporeal system to the vascular system of the individual to be treated. Conventional alternatives are arteriovenous (AV), venovenous (VV) and venoarterial (VA) types of connection, with which in each case the direction of blood flow is described, based on the corporeal vascular system. For example, an arteriovenous connection describes an extracorporeal system which takes arterial blood from the individual's body and—if necessary after appropriate treatment—returns it to the venous system of the body. AV and VV connections are usually preferred in the area of hemodialysis and hemofiltration. Whereas extracorporeal VV and VA systems are usually operated with an external pump, this is unnecessary with extracorporeal AV systems—provided the arterial blood pressure is sufficient. The dosage of anticoagulant agents and adjuvant anticoagulants may be different with different types of connection, for example higher dosages may be necessary on use of pumps.

The access to the corporeal vascular system can be achieved for example by introducing tubular inlet lines into corporeal vessels. Suitable examples are cannulas or catheters, whose dimensions, that is to say in particular length and internal diameter, can be adapted to the particular system. For example, short and wide-lumen catheters are preferred for AV systems, and double-lumen catheters are preferred for W systems. Normally so-called shunts are used as appropriate access to the corporeal vascular system, for example in the form of artificial vascular implants or fistulas.

In certain cases, the blood is passed along or through filters or membranes. It may be necessary to choose the membrane according to the anticoagulant agent. The use according to the invention of PEG-hirudin is suitable for conventional membrane and filtration systems employed in particular in the area of hemodialysis and hemofiltration. These include membranes of natural materials such as cellulose derivatives, for example cellulose triacetate, and synthetic materials, for example polysulfones, polyamides, polyacrylonitrile. Plate filters and hollow fiber arrangements are examples of possible geometries one advantage of the use of PEG-hirudin is that it is suitable both for extracorporeal systems with HF membranes (high flux) and for those with LF membranes (low flux). A further advantage is that PMMA membranes, for example the membranes made of poly(methyl methacrylate) or poly(methyl methacrylate) copolymers described in DE 197 15 504 A1, for example the Toray membrane known for this purpose) [sic] can, because of their particular binding properties for PEG-hirudin, be used as functional antidote for rapid elimination of PEG-hirudin, for example in cases of intolerance reactions or overdosage.

The purpose of the use according to the invention of anticoagulant agents is, in addition to that as anticoagulant during the extracorporeal circulation, the prophylaxis of vascular complications after the extracorporeal circulation.

Vascular complications include according to the invention disturbances of the function of the cerebral, cardiac, mesenteric and peripheral vessels and pathological states associated therewith and symptoms thereof. These include, for example, the formation of thrombi in the vascular system of the individual to be treated, that is to say, in particular, venous and arterial thromboses, in particular deep vein thromboses, peripheral occlusive diseases, shunt thromboses, catheter thromboses, thromboembolisms, myocardial infarct, unstable angina pectoris and stroke. Accordingly, the use according to the invention of anticoagulant agents has particular advantages in individuals at increased risk of vascular complications. Risk-increasing factors include both disorders of the coagulation system, in particular AT-III deficits and elevated fibrinogen levels, thrombocytosis, HIT, and hypertension and preexistent disorders such as coronary heart diseases, diabetes or other vascular disorders.

The use according to the invention of anticoagulant agents for the prophylaxis of vascular complications extends at least over a period which is subsequent to the time of the extracorporeal circulation and, according to a particular embodiment of the present invention, follows it directly. In the case of a multiple, i.e. periodically interrupted, extracorporeal circulation, that is to say, in particular, a periodic sequence of extra- and intracorporeal phases, this period ideally extends until the next extracorporeal phase. According to a particular embodiment of the present invention, anticoagulant agents are used for treatment of an individual with multiple alternation of extra- and intracorporeal phase as anticoagulant during the extracorporeal phases and for the prophylaxis of vascular complications during the intracorporeal phases. For the sake of completeness, it may be stated that the use as anticoagulant during the extracorporeal phase may likewise include a prophylactic treatment of vascular complications, and this is also usually the case.

The use according to the invention of anticoagulant agents comprises a method within the framework of the treatment. This entails administering to the individual to be treated, preferably a mammal, in particular a human, agricultural animal or domestic animal, an appropriate amount of one or more anticoagulant agents, usually formulated in accordance with human pharmaceutical or veterinary practice.

The administration of anticoagulant agents can take place in accordance with a—usually necessary—systemic agent administration. Of the possible administration routes, a convenient possibility for administering an appropriate amount of anticoagulant agents is the parenteral route and, in particular, injection with the blood front into the dialysis system, in particular via an introduction means.

With a view to the extracorporeal circulation, expediency of the amount of anticoagulant agents to be administered is determined in particular by the anticoagulant effect of the resulting blood levels. According to one aspect of the present invention, values in the therapeutic range are expedient. Therapeutic means here an effect which is able to counteract the thrombotic stimuli occurring during the extracorporeal circulation. Advantageous in this sense are blood levels based on anti-IIa of at least about 400 ng/ml, preferably of at least about 500 ng/ml and, in particular, of at least about 600 ng/ml. Measurement of the APTT shows an APTT prolonged advantageously at least about 1.3-fold, preferably at least about 1.6-fold and, in particular, at least about 1.8-fold. Measurement of the ECT shows an ECT prolonged advantageously at least about 1.2-fold, preferably at least about 1.6-fold and, in particular, at least about 1.8-fold.

According to a further aspect of the present invention, expedient values are those which keep the risk of bleeding by the treated individual within limits. In this sense, it is a further advantage for the blood levels to be, about 5 minutes after administration, a maximum of about 2400 ng/ml, preferably a maximum of about 1700 ng/ml and, in particular, a maximum of about 1500 ng/ml, based on anti-IIa. Measurement of the APTT shows an APTT prolonged advantageously by a maximum of about 5.0-fold, preferably by a maximum of about 3.3-fold and, in particular, by a maximum of about 2.7-fold. Measurement of the ECT shows an ECT prolonged advantageously by a maximum of about 5.5-fold, preferably by a maximum of about 4.5-fold and, in particular, by a maximum of about 4.0-fold.

The abovementioned values need not—where medically justifiable—be maintained throughout the extracorporeal phase. According to an advantageous embodiment of the present invention, the amount of anticoagulant agent to be administered is such that the aforementioned minimum blood levels are obtained when the extracorporeal circulation is completed. According to a further advantageous embodiment of the present invention, the abovementioned values apply to the period which is limited on the one hand by the reaching of a maximum blood level, and on the other hand by the completion of the extracorporeal phase.

The time of adminstration of an anticoagulant agent and, where appropriate, further anticoagulants is expediently chosen so that an anticoagulant effect is ensured even in the initial phase of the extracorporeal circulation. For this purpose the administration can take place before connection to the extracorporeal system. Administration directly on connection to the extracorporeal system is also possible and may in this case conveniently take place via the extracorporeal system. If administration takes place directly on connection to the system, this usually takes place with the blood front or—where the residual level of anticoagulant agent in the patient permits this from the medical viewpoint—shortly thereafter. Administration via the extracorporeal system is to be included according to the invention within the term parenteral administration and—in the case of a venous connection to the extracorporeal system—in particular within the term intravenous administration.

With a view to the treatment according to the invention after the extracorporeal circulation, the expediency of the amount of PEG-hirudin to be administered will be determined in particular by the prophylactic effect of the resulting blood levels. A prophylactic effect is in this connection an antithrombotic effect, which can be adapted to the relatively weak thrombotic stimulus after the extracorporeal circulation. For the period of an intracorporeal treatment phase it is possible and expedient usually to choose blood levels which are lower than the blood levels obtained during the extracorporeal circulation. According to one aspect of the present invention, values in the range with prophylactic activity are possible—measured by the therapeutic blood levels obtained during the extracorporeal circulation. Advantageous in this sense are blood levels of anticoagulant agents, based on anti-IIa, after the extracorporeal circulation of at least about 150 ng/ml, preferably of at least about 300 ng/ml and, in particular, of at least about 400 ng/ml. Measurement of the APTT shows an APTT prolonged advantageously at least about 1.2-fold, preferably at least about 1.3-fold and, in particular, at least about 1.5-fold. Measurement of the ECT shows an ECT prolonged advantageously at least about 1.1-fold, preferably at least about 1.3-fold and, in particular, at least about 1.4-fold. In particular, the blood levels during an intracorporeal phase vary between the blood level present on completion of the extracorporeal circulation and the abovementioned minimum values. The blood levels normally decrease as a function of time.

These values need not necessarily be maintained throughout the intracorporeal phase either. According to another advantageous embodiment of the present invention, the amount of anticoagulant agent to be administered is such that, with a periodic sequence of extra- and intracorporeal phases, the blood levels obtained at the end of the intracorporeal phases are at least about 150 ng/ml, preferably at least about 300 ng/ml and, in particular, at least about 400 ng/ml, based on anti-IIa. Measurement of the APTT shows an APTT prolonged advantageously at least about 1.2-fold, preferably at least about 1.3-fold and, in particular, at least about 1.5-fold. Measurement of the ECT shows an ECT prolonged advantageously at least about 1.1-fold, preferably at least about 1.3-fold and, in particular, at least about 1.4-fold. On the other hand, blood levels advantageous at this time are a maximum of about 1000 ng/ml, preferably a maximum of about 700 ng/ml and, in particular, a maximum of about 600 ng/ml, based on anti-IIa. Measurement of the APTT shows an APTT prolonged advantageously by a maximum of about 3.5-fold, preferably by a maximum of about 2.8-fold and, in particular, by a maximum of about 2.5-fold. Measurement of the ECT shows an ECT prolonged advantageously by a maximum of about 4.0-fold, preferably by a maximum of about 3.0-fold and, in particular, by a maximum of about 2.5-fold.

Depending on the therapeutic blood levels present on completion of the extracorporeal circulation, only after a certain transitional period following the extracorporeal circulation are subtherapeutic blood levels usually obtained. The transitional period from therapeutic to subtherapeutic and, in particular, prophylactic blood levels depends on the natural or, where appropriate, artificial elimination of anticoagulant agents from the blood of the treated individual.

A particular aspect of the present invention comprises the treatment of individuals with renal insufficiency. Renal insufficiency means according to the invention that the elimination efficiency of the kidney is inadequate or absent. These include, in particular, individuals with a creatinine clearence [sic] $CL_{CR}$ of less than 100 ml/min, especially less than 50 ml/min and, in particular, less than 10 ml/min.

According to one embodiment of the present invention, individuals with acute renal insufficiency, i.e. with the elimination efficiency of the kidney temporarily inadequate or absent are treated. In this case, the blood of the affected individual undergoes extracorporeal treatment until an adquate renal elimination efficiency is restored. The duration of the extracorporeal phase naturally varies from case to case, averaging several days. This type of treatment is referred to according to the invention as continuous hemofiltration. The treatment duration of at least about 3 days and, in particular, of at least about 5 days represents a particular embodiment of the present invention.

A further particular embodiment of the present invention is directed at the treatment of individuals with chronic renal insufficiency. These are individuals whose renal elimination efficiency is permanently inadequate or absent. In this case, the extracorporeal circulation is a regular event. Both the duration of extracorporeal phases and the gaps between the extracorporeal phases which, according to a particular embodiment of the present invention, correspond to the intracorporeal treatment phases are adapted to the condition of the individual, in particular taking account of any remaining renal elimination efficiency. The present invention is directed in particular at the treatment of individuals with at least one extracorporeal circulation a week and, in particular, at individuals with advanced chronic renal insufficiency and, accordingly, on average at least about two and, in particular, about three, extracorporeal circulations a week. This type of treatment is referred to according to the invention as intermittent (periodic) hemodialysis and represents, according to a particular embodiment of the present invention, a long-term, treatment consisting of alternate extra- and intracorporeal treatment phases.

Within the scope of this embodiment relating to intermittent hemodialysis it is possible for expedient blood levels to be reached by administering an appropriate amount of anticoagulant agent per cycle as a single dose or through several doses. According to a particular embodiment of the present invention, the anticoagulant agent is administered in the form of a single dose per cycle, and thus once per hemodialysis.

A cycle is composed of an extracorporeal and an intracorporeal phase. The administration expediently takes place, especially in the case of a single dose, at the start of a cycle, i.e. at the start of an extracorporeal phase. However, it may also take place at another time during a cycle, for example after completion of the extracorporeal circulation. The amount of the single dose, preferably as bolus, can advantageously be such that another dose of anticoagulant agent is given at the start of the next cycle in each instance. A possible basis for the amount of each single dose is a blood level of the anticoagulant agent measured before the start of each cycle. The corresponding blood level is then raised through the administration of the single dose. It reaches a maximum which is within a range appropriate for the purose of an anticoagulant measure. Advantageous blood levels about 5 minutes after administration are at least about 600 ng/ml, preferably at least about 700 ng/ml and, in particular, at least about 800 ng/ml, based on anti-IIa. Measurement of the APTT shows an APTT prolonged advantageously at least about 1.5-fold, preferably at least about 1.9-fold and, in particular, at least about 2.3-fold. Measurement of the ECT shows an ECT prolonged advantageously at least about 1.5-fold, advantageously at least about 2.0-fold and, in particular, at least about 2.5-fold.

On the other hand, to take account of the risk of bleeding, these maxima should be kept as low as possible. One advantage of the use of PEG-hirudin is that these maxima can be less than about 2400 ng/ml, preferably less than about 1700 ng/ml and, in particular, less than about 1500 ng/ml, based on anti-IIa. Thus, the APTT can be prolonged less than about 5.0-fold, preferably less than about 3.3-fold and, in particular, less than about 2.7-fold, and the ECT can be prolonged less than about 5.5-fold, preferably less than about 4.5-fold and, in particular, less than about 4.0-fold.

The blood levels decrease as a function of time during the extracorporeal phase. The blood levels advantageously remain in the therapeutic range during the extracorporeal phase. The blood levels mentioned above in this connection are advantageous here too. On the other hand, advantageous blood levels on completion of the extracorporeal phase are a maximum of about 2000 ng/ml, preferably a maximum of about 1500 ng/ml and, in particular, a maximum of about 1100 ng/ml, based on anti-IIa. Measurement of the APTT shows an APTT prolonged advantageously by a maximum of about 4.5-fold, preferably by a maximum of about 3.0-fold and, in particular, by a maximum of about 2.5-fold.

Measurement of the ECT shows an ECT prolonged advantageously by a maximum of about 4.0-fold, preferably by a maximum of about 3.5-fold and, in particular, by a maximum of about 3.0-fold.

It is possible according to the invention for the single dose to remain essentially the same on use of anticoagulant agents in the framework of intermittent hemodialysis. Accordingly, an amount of anticoagulant agent which remains essentially constant from cycle to cycle is administered to an individual. This amount can be based on individual parameters, in particular those influencing the dosage, for example, the body weight of the individual to be treated, but it is also possible to use a fixed dose per individual. However, account must be taken of the fact that adaptation to the anticoagulant agent used according to the invention may be necessary at the start of therapy. Thus, for example, a relatively high dose must be chosen at the start of regular administration of PEG-hirudin to patients with chronic renal insufficiency in order to obtain expedient blood levels. The dosage can then be kept from cycle to cycle at a level which remains essentially constant during the subsequent regular administration of PEG-hirudin. The adaptation phase usually comprises several cycles, preferably less than 15 and, in particular, less than 10, it being possible advantageously to choose after about 5 cycles a dosage which is a maximum of about +/- 25% or, in particular, +/- 10% and preferably essentially at the desired constant dosage.

If the anticoagulant agents are administered in a dosage which remains essentially the same, the monitoring of the individual can be confined to checking the particular blood level before an extracorporeal phase and, where appropriate, checking the particular blood level after administration of the single dose. The former check serves in particular as a basis for the amount of the necessary dosage, and the latter to avoid an increased risk of bleeding due to any excessive maximum blood levels. It may be mentioned in this connection that the use of PEG-hirudin advantageously provides a possibility of eliminating PEG-hirudin efficiency from the blood of an individual. Reference is made to the membranes which are described above and are known for this purpose.

According to a particular embodiment of the present invention, the amount of the single dose preferably administered at the start of a hemodialysis is such that the concentration of anticoagulant agent varies in a range from about 400 ng/ml to about 2400 ng/ml, preferably in a range from about 500 ng/ml to about 1700 ng/ml and, in particular, in a range from about 600 ng/ml to about 1500 ng/ml, based on anti-IIa, during the hemodialysis. In this sense, the measured APTT is prolonged in a range of about 1.3-fold to about 5.0-fold, preferably in a range from about 1.6-fold to about 3.3-fold and, in particular, in a range from about 1.8-fold to about 2.7-fold, or the measured ECT is prolonged in a range from about 1.2-fold to about 5.5-fold, preferably in a range from about 1.6-fold to about 4.5-fold and, in particular, in a range from about 1.8-fold to about 4.0-fold.

According to a n other particular embodiment of the present invention, the amount of the single dose administered for a hemodialysis is such that the concentration of anticoagulant agent after completion of a hemodialysis and until the next one varies in the range from about 2000 ng/ml to about 150 ng/ml, preferably in a range from about 1500 ng/ml to about 300 ng/ml and, in particular, in a range from about 1100 ng/ml to about 400 ng/ml, based on anti-IIa. In this sense, the measured APTT is prolonged in a range from about 4.5-fold to about 1.2-fold, preferably in a range from about 3.0-fold to about 1.3-fold and, in particular, in a range from about 2.5-fold to about 1.5-fold, or the measured ECT is prolonged in a range from about 4.5-fold to about 1.1-fold, preferably in a range from about 3.5-fold to about 1.3-fold and, in particular, in a range from about 3.0-fold to about 1.4-fold.

Within the scope of the particular embodiments of the present invention which are described above, the amount of the single dose administered for a hemodialysis can advantageously be such that, about 5 minutes after administration, the concentration of anticoagulant agent is at least about 600 ng/ml, preferably at least about 700 ng/ml and, in particular, at least about 800 ng/ml, based on anti-IIa. Measurement of the APTT shows an APTT prolonged advantageously by at least about 1.5-fold, preferably by at least about 1.9-fold and, in particular, by at least about 2.3-fold measurement of the ECT shows an ECT prolonged advantageously by at least about 1.5-fold, preferably by at least about 2.0-fold and, in particular, by at least about 2.5-fold.

The blood levels described above can usually be obtained with bolus doses in the range from about 2000 to about 1400 ATU/kg, preferably from about 400 ATU/kg to about 1200 ATU/kg and, in particular, from about 600 ATU/kg to about 1000 ATU/kg, of body weight. After adaptation it is possible to treat individuals with chronic renal insufficiency, with an average of three exracorporeal circulations a week, with a dosage of about 200 to about 1000 ATU/kg, preferably about 200 ATU/kg to about 800 ATU/kg and, in particular, from about 400 ATU/kg to about 600 ATU/kg, of body weight. The abbreviation ATU stands for antithrombin units bas ed on the WHO I thrombin standard.

In particular, an individual with chronic renal insufficiency can be treated, with an average of three extracorporeal circulations a week, with a dosage of about 0.02 to about 1.0 mg of PEG-hirudin and, after adaptation, with a dosage of about 0.03 to about 0.06 mg, in each case based on kg of body weight, on use of a PEG-hirudin with a specific activity of about 10,000 to 14,000 ATU/mg of protein and, in particular, a specific activity of about 13,350 ATU/mg of protein.

The invention also relates to the use of anticoagulant agents for producing pharmaceutical compositions for the treatment according to the invention. Thus, anticoagulant agents are usually administered in the form of pharmaceutical compositions which, besides the agent, comprise at least one pharmaceutically suitable excipient.

Appropriate for parenteral administration, the pharmaceutical compositions are preferably administered as liquid pharmaceutical form. Agent solutions in aqueous media such as water or physiological saline are particularly preferred.

For practical use, anticoagulant agents, in particular PEG-hirudin, can be supplied in solid, especially lyophilized, form and, separately therefrom, the solvent. Agent and solvent can be packed in aliquots in suitable containers, for example vials, which makes reconstitution of a solution of known concentration conveniently possible. Suitable with a view to the preferred dosages described above are, for example, 2 or 10 ml containers respectively containing 5 to 50 mg of PEG-hirudin; vials containing 50 mg of PEG-hirudin can be supplied as multiple-dose containers (reconstitution of the agent with a preserved solution).

The term blood level refers to a particular amount of anticoagulant agent(s) in the blood of an individual, which, on use of the determination methods described in the reference examples, can be expressed by one or, where appropriate, even several of the stated activity values.

The stated concentrations of anticoagulant agents based on anti-IIa relate to the protein content of the PEG-hirudin used. Equivalent amounts apply to other substances with anti-IIa activity.

Measurement of the ECT (ecarin clotting time) refers according to the invention to the use of direct thrombin inhibitors.

The stated blood levels represent average values which relation to a group of at least about 10 individuals. Thus, because of the biological variability, the value for a single individual will usually differ from the stated statistical average within the framework of the statistical assessment and nevertheless be assignable to the average.

The stated blood levels are guideline values which may vary within the scope of the accuracy of measurement even in relation to the same measurement sample. Accuracies of measurement for the individual determination methods are indicated in the reference examples. This variation is expressed by the "about" prefixing each value.

The intention of the following example is to illustrate the invention without restricting it thereto.

EXAMPLE

Treatment of dialysis patents with PEG-hirudin 20 male and female patients between 18 and 75 years who must regularly undergo hemodialysis were selected. After an initial treatment with heparin (UFH), each patient was given an intravenous injection, immediately before the first dialysis during PEG-hirudin treatment, of a dose of 0.08 mg/kg of PEG-hirudin with a specific antithrombin activity of 13,354 ATU/mg of protein per kg of body weight. This was followed by hemodialysis with an average duration of 4 hours, 3×a week using a Hemophan low flux membrane in a GFS plus 16 dialyzer. When the dialysis was complete and before the subsequent dialysis sessions, firstly the PEG-hirudin concentrations in the patient's blood were determined. The measured values served as the basis for the amount of the PEG-hirudin doses to be administered immediately before each hemodialysis. The residual PEG-hirudin concentrations initially increased and allowed the dose to be reduced from the initial 0.08 mg/kg of body weight to 0.03 to 0.05 mg/kg of body weight. It emerged that this dosage was suitable for obtaining blood levels of PEG-hirudin in the range from about 500 to about 1000 ng/ml of whole blood on completion of each dialysis with th r ee hemodialyses a week. The residual PEG-hirudin concentration in the blood of each patient between the hemodialysis sessions ensured prophylactic protection against vascular complications.

The results are compiled in Tables 1 to 3.

THE DRAWINGS SHOW

Figure 2:
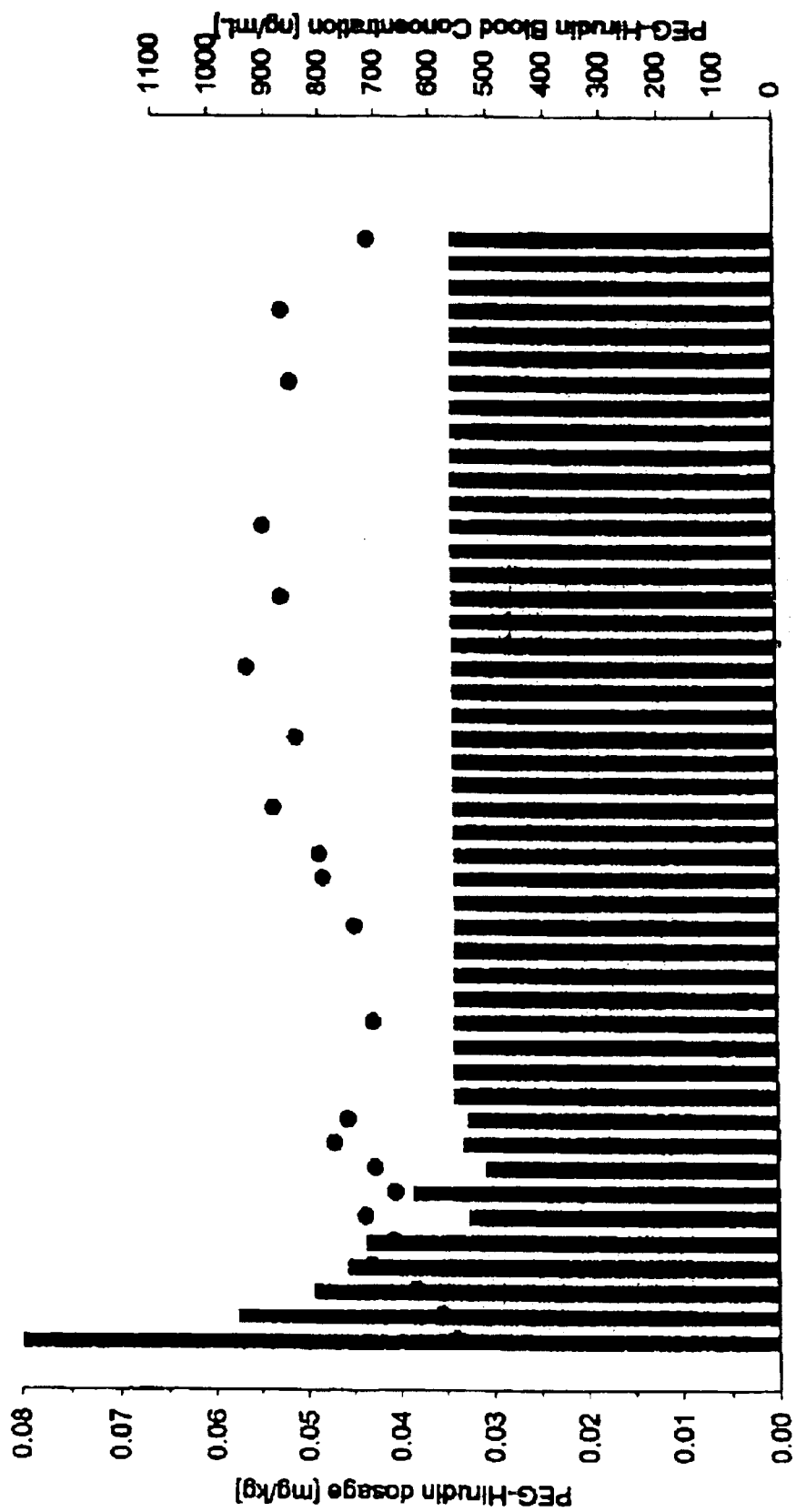
Figure 3:
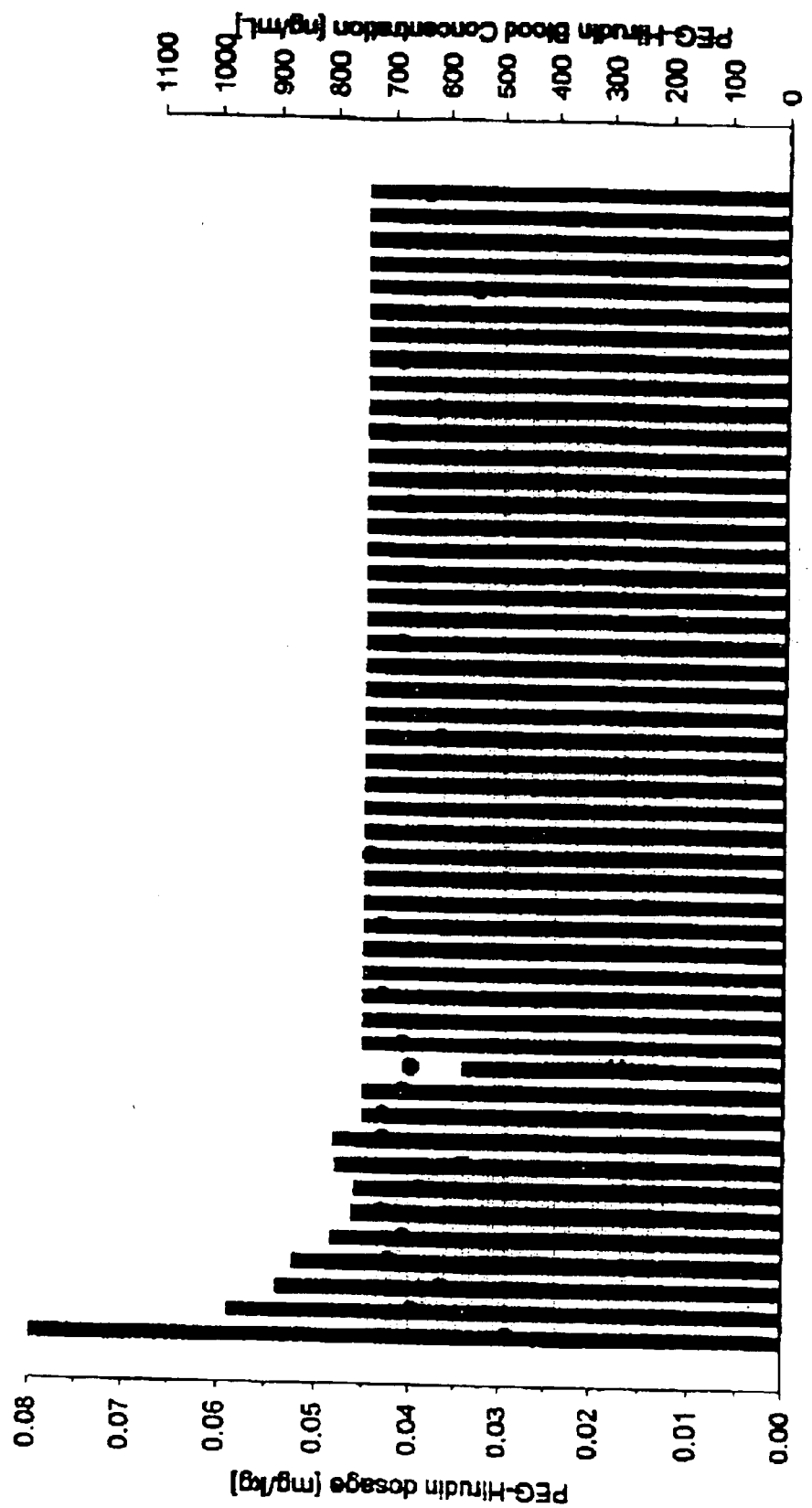
Figure 4:
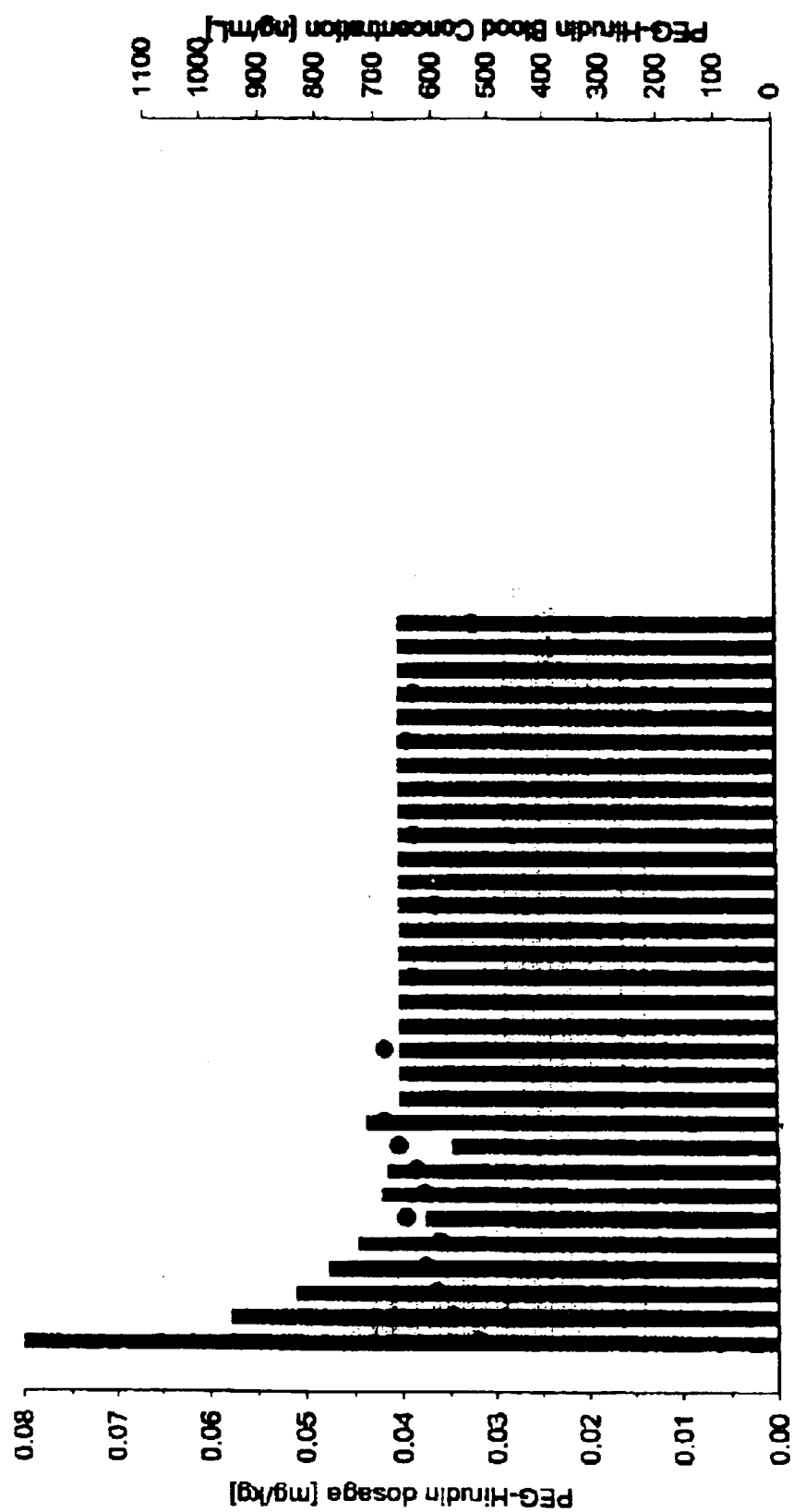

FIG. 1 by the example of patient 15 the PEG-hirudin doses (bars) administered for dialyses 1 to 50, and the blood levels of PEG-hirudin (dots) measured after some dialysis sessions;

FIG. 2 by the example of patient 16 the PEG-hirudin doses (bars) administered for dialyses 1 to 47, and the blood levels of PEG-hirudin (dots) measured after some dialysis sessions;

FIG. 3 by the example of patient 18 the PEG-hirudin doses (bars) administered for dialyses 1 to 49, and the blood levels of PEG-hirudin (dots) measured after some dialysis sessions;

FIG. 4 by the example of patient 20 the PEG-hirudin doses (bars) administered for dialyses 1 to 31, and the blood levels of PEG-hirudin (dots) measured after some dialysis sessions.

TABLE 1

APTT determination

| No. of the dialysis | APTT Before dialysis [ratio] | APTT Bolus 5' after admin. [ratio] | APTT After dialysis [ratio] |
|---|---|---|---|
| 01-UFH | 1.0 | 6.9 (4.2–8.8) | 1.3 (0.9–2.0) |
| 02-UFH | 1.0 | — | 1.4 (0.9–2.9) |
| 03-UFH | 1.0 | — | 1.3 (0.9–2.0) |
| 04-PEG-Hirudin | 1.0 | 2.5 (2.4–2.6) | 2.2 (1.8–2.6) |
| 05-PEG-Hirudin | 1.7 (1.5–2.0) | — | 2.3 (1.9–3.1) |
| 06-PEG-Hirudin | 1.9 (1.8–2.3) | — | 2.3 (2.0–2.7) |
| 07-PEG-Hirudin | 1.9 (1.6–2.4) | — | 2.2 (1.9–2.6) |
| 08-PEG-Hirudin | 2.0 (1.7–2.4) | 2.6 (2.3–3.1) | 2.5 (2.0–3.6) |
| 09-PEG-Hirudin | 2.0 (1.8–2.4) | — | 2.4 (2.0–3.4) |
| 10-PEG-Hirudin | 2.0 (1.8–2.4) | — | 2.3 (2.0–3.2) |
| 11-PEG-Hirudin | 2.0 (1.7–2.3) | — | 2.3 (2.0–2.6) |
| 12-PEG-Hirudin | 2.0 (1.6–2.3) | — | 2.3 (1.9–2.9) |
| 13-PEG-Hirudin | 1.9 (1.5–2.2) | 2.5 (2.3–2.7) | 2.2 (2.0–2.5) |

TABLE 2

Anti-IIa activity determination

| No. of the dialysis | Anti-IIa Before dialysis [ng/ml] | Anti-IIa Bolus 5' after admin. [ng/ml] | Anti-IIa After dialysis [ng/ml] |
|---|---|---|---|
| 01-UFH | | | |
| 02-UFH | | | |
| 03-UFH | | | |
| 04-PEG-Hirudin | 0 | 1298 (925–1532) | 818 (660–958) |
| 05-PEG-Hirudin | 275 (197–322) | — | 842 (586–1100) |
| 06-PEG-Hirudin | 426 (275–539) | — | 942 (733–1201) |
| 07-PEG-Hirudin | 432 (237–627) | — | 953 (681–1242) |
| 08-PEG-Hirudin | 536 (448–699) | 1240 (910–1436) | 951 (704–1288) |
| 09-PEG-Hirudin | 518 (326–674) | — | 995 (758–1691) |
| 10-PEG-Hirudin | 462 (344–555) | — | 956 (685–1735) |
| 11-PEG-Hirudin | 516 (438–654) | — | 950 (648–1679) |
| 12-PEG-Hirudin | 491 (373–677) | — | 878 (688–1243) |
| 13-PEG-Hirudin | 487 (276–614) | 1076 (789–1270) | 834 (584–1133) |

TABLE 3

ECT determination

| No of the dialysis | ECT Before dialysis [ratio] | ECT Bolus 5' after admin. [s] [ratio] | ECT Before dialysis [ng/ml] [ratio] |
|---|---|---|---|
| 01-UFH | | | |
| 02-UFH | | | |
| 03-UFH | | | |

TABLE 3-continued

ECT determination

| No of the dialysis | ECT Before dialysis [ratio] | ECT Bolus 5' after admin. [s] [ratio] | ECT Before dialysis [ng/ml] [ratio] |
|---|---|---|---|
| 04-PEG-Hirudin | 1.0 | 3.0 (2.7–3.9) | 2.3 (2.0–2.5) |
| 05-PEG-Hirudin | 1.6 (1.4–1.7) | — | 2.4 (2.0–2.7) |
| 06-PEG-Hirudin | 1.8 (1.6–2.0) | — | 2.5 (2.3–2.7) |
| 07-PEG-Hirudin | 1.9 (1.6–2.0) | — | 2.5 (2.2–2.8) |
| 08-PEG-Hirudin | 1.9 (1.8–2.1) | 3.1 (2.7–3.4) | 2.6 (2.2–2.8) |
| 09-PEG-Hirudin | 2.1 (1.7–2.3) | — | 2.6 (2.4–2.9) |
| 10-PEG-Hirudin | 2.0 (1.8–2.2) | — | 2.6 (2.4–2.7) |
| 11-PEG-Hirudin | 2.1 (2.0–2.2) | — | 2.6 (2.3–3.0) |
| 12-PEG-Hirudin | 2.1 (1.8–2.4) | — | 2.6 (2.4–2.8) |
| 13-PEG-Hirudin | 2.0 (1.8–2.3) | 3.1 (2.7–3.5) | 2.6 (2.3–2.8) |

Reference Example 1
APTT determination

The determination of the activated partial thromboplastin time (APTT) is based on plasma fibrin formation induced by addition of a partial thromboplastin (Actin FS) and calicum [sic] ions to the plasma. Ellagic acid is used as activator.

9 volumes of venous blood+1 volume of citrate (0.13 mol/l) are cautiously mixed and centrifuged at 1600×g and 2–10° C. for 10 min. The sample volume is at least 450 µl. Samples are dispatched if necessary in the frozen state, and samples are stored in freezers.

The controls used are control plasma in the normal range, control plasma in the therapeutic range, control plasma in the low therapeutic range and a quality control in the normal range, for example the controls commercially available from Dade citrol 1, Citrol 2, Citrol 3 and Coag Trol N.

The measurement is carried out in an ACL 3000.

The ACL 3000 is a completely automatic, microcomputer-controlled centrifugal analysis system. After the start of the analysis cycle, sample and Actin are pipetted separately into the half-cuvettes of a reaction rotor made of acrylic glass with 20 cuvettes, and are mixed and then incubate d. After the incubation, calcium chloride is pipetted into the cuvettes, mixed and measured. Measurements are carried out while the rotor is rotating. The light source for the nephelometric measurement is a light-emitting diode (LED) whose light beam is directed via a light guide system ($\gamma$=660 nm) onto the measuring cuvettes. The scattered light distribution is measured at an angle of 90° to the light source with the aid of a semiconductor sensor located underneath the rotor carrier. The measured results can also be stated as ratio and describe the ratio of the current value to the individual baseline value for a patient before the dialysis with PEG-hirudin.

The accuracy of measurement is +10% to −10%.

Reference Example 2
Anti-IIa activity determination

Determination of the anti-IIa activity is based on measurement of the activity remaining after addition of excess thrombin to the sample. Heparin and other non-thrombin serine proteases are neutralized before the assay by adding prothamine [sic] chloride and aprotinin to the sample. Remaining thrombin cleaves the chromogenic substrate S2238 which is added to the sample.

9 volumes of venous blood and 1 volume of citrate (0.13 mol/l) are cautiously mixed and centrifuged at 1600×g and 2–10° C. for 10 min. The sample volume is about 100 µl. Samples are dispatched if necessary in the frozen state, and samples are stored in freezers.

The following standards are used in the PEG-hirudin determination:

Standard A: PEG-hirudin concentration [c]=26.6 mg/ml; specific activity of 11,696 ATU/mg of protein Standard B: [c]=500 µg/ml (1:53.3 dilution of standard A with 0.5% BSA)

Standard C: [c]=50 µg/ml (1:10 dilution of standard B with 0.5% BSA)

Standard D: [c]=1000 ng/ml (1:50 dilution of standard C with normal human citrated plasma)

Standard B–D are stored in aliquots in the frozen state before use.

Calibration samples with concentrations of 100, 200, 400, 600 and 800 mg/ml [sic] are prepared by suitable dilution of standard D with normal human citrated plasma.

This method can be standardized correspondingly for determination of other anticoagulant agents.

The measurement is carried out in an ACL 3000 (incubation time: 120 s; inter-ramp interval: 3 s; delay time: 3 s; aquisition time: 120 s; speed: 600 rpm). The extinction is measured using a 405 nm filter at a constant rotor speed.

The accuracy of measurement is +20 to −10%.

Reference Example 3
ECT determination

Determination of the ECT (ecarin clotting time) is based on the inhibition of the coagulation activity of meizothrombin. Ecarin, a purified fraction of Echis carinatus venom, produces meizothrombin by cleavage of the prothromin in the plasma. The time until fibrinogen coagulates induced by ecarin is measured.

9 volume [sic] of venous blood and 1 volume of citrate (0.13 mol/l) are cautiously mixed. The sample volume is about 100 µl. Samples are dispatched if necessary in the frozen state, and samples are stored in freezers.

The following standards are used in the PEG-hirudin determination:

Standard A: PEG-hirudin concentration [c]=26.6 mg/ml; specific activity of 11,696 ATU/mg of protein Standard B: [c]=500 µg/ml (1:53.3 dilution of standard A with 0.5% BSA)

Standard C: [c]=50 µg/ml (1:10 dilution of standard B with 0.5% BSA)

Standard E: [c]=2500 ng/ml (1:20 dilution of standard C with normal human citrated plasma)

Standard B–E are stored in aliquots in the frozen state before use.

Calibration samples with concentrations of 250, 500, 1500, 2000 and 2500 mg/ml [sic] are prepared by suitable dilution of standard E with normal human citrated plasma.

This method can be standardized correspondingly for determination of other anticoagulant agents.

The measurement is carried out in an ACL 3000 (incubation time: 120 s; inter-ramp interval: 3 s; delay time: 3 s; aquisition time: 800 s; speed: 1200 rpm).

The measured results can also be stated as ratio and describe the ratio of the current value to the individual baseline value for a patient before the dialysis with PEG-hirudin.

The accuracy of measurement is +30% to −10%.

Reference Example 4
Determination of the terminal half-life $\tau_{1/2}$

The terminal half-life $\tau_{1/2}$ is calculated from $0.693/\lambda_z$. $\lambda_z$ represents the terminal rate of elimination which is determined by linear regression of a logarithmic plot of the concentration of the relevant agent in the blood against time as terminal slope of the concentration-time curve. For example, based on the time-dependent change in concentration indicated in Table 4 below, $\lambda_z$ can be calculated to be 0.086 1/h and $\tau_{1/2}$ can be calculated to be 8.04 h.

TABLE 4

| Time [h] | Concentration [nmol/l] |
|---|---|
| 0 | 0 |
| 0.1667 | 143 |
| 0.3333 | 256 |
| 0.5 | 213 |
| 0.6667 | 193 |
| 0.8333 | 171 |
| 1 | 139 |
| 1.483 | 123 |
| 2 | 93 |
| 4 | 58 |
| 6 | 38 |
| 7.983 | 23 |
| 9.983 | 34 |
| 11.98 | 30 |
| 15.97 | 20 |
| 24.03 | 9 |
| 28 | 8 |
| 32.17 | 5 |

We claim:

1. A method of treating an individual suffering from chronic renal insufficiency, which comprises subjecting said individual to intermittent hemodialysis comprising repeating cycles of an extracorporeal phase wherein blood of said individual is circulated extracorporeally, and an intracorporeal phase wherein no blood of said individual is circulated extracorporeally, and administering to said individual an effective amount of PEG(polyethylene glycol)-hirudin, said effective amount being adapted to provide for an effective anticoagulant protection during the extracorporeal phase, and for an effective prophylaxis of vascular complications during the intracorporeal phase.

2. The method of claim 1, wherein the PEG-hirudin is administered such that, at the end of the intracorporeal phase, a PEG-hirudin blood level having at least a value of about 150 ng/ml is obtained.

3. The method of claim 1, wherein the PEG-hirudin is administered such that, at the end of the intracorporeal phase, a PEG-hirudin blood level having at least a value of about 300 ng/ml is obtained.

4. The method of claim 1, wherein the effective amount is administered in form of a single dose per cycle.

5. The method of claim 4, wherein the single dose is administered at the start of the extracorporeal phase.

6. The method of claim 4, wherein the effective amount is adapted such that, during the intracorporeal phase, a PEG-hirudin blood level of about 150 ng/ml to 2000 ng/ml is obtained.

7. The method of claim 4, wherein the effective amount is adapted such that the activated thromboplastic time (APTT) is prolonged about 2.7-fold to about 1.8-fold during the extracorporeal phase.

8. The method of claim 4, wherein the effective amount is adapted such that the APTT is at least prolonged about 1.2-fold during a hemodialysis cycle.

9. The method of claim 1, wherein the PEG-hirudin is derived from recombinant hirudin.

SEQUENCE LISTING

<160> NUMBER OF SEQ ID NOS: 1

<210> SEQ ID NO 1
<211> LENGTH: 65
<212> TYPE: PRT
<213> ORGANISM: Artificial Sequence
<220> FEATURE:
<223> OTHER INFORMATION: Description of Artificial Sequence: recombinant
      hirudin mutein

<400> SEQUENCE: 1

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
                20                  25                  30

Lys Gly Glu Arg Asn Gln Cys Val Thr Gly Glu Gly Thr Pro Arg Pro
            35                  40                  45

Gln Ser His Asn Asp Gly Asp Phe Glu Glu Ile Pro Glu Glu Tyr Leu
        50                  55                  60

Gln
65

* * * * *